(12) United States Patent
Granoff et al.

(10) Patent No.: US 8,663,940 B2
(45) Date of Patent: Mar. 4, 2014

(54) EX-VIVO PASSIVE PROTECTION BACTEREMIA ASSAY

(75) Inventors: Dan M. Granoff, Berkeley, CA (US); Jo Anne Welsch, Berkeley, CA (US); Joyce Plested, Oakland, CA (US)

(73) Assignee: Children's Hospital & Research Center Oakland, Oakland, CA (US)

( * ) Notice: Subject to any disclaimer, the term of this patent is extended or adjusted under 35 U.S.C. 154(b) by 0 days.

(21) Appl. No.: 13/133,907

(22) PCT Filed: Dec. 10, 2009

(86) PCT No.: PCT/US2009/067515
§ 371 (c)(1),
(2), (4) Date: Sep. 8, 2011

(87) PCT Pub. No.: WO2010/074991
PCT Pub. Date: Jul. 1, 2010

(65) Prior Publication Data
US 2011/0312020 A1 Dec. 22, 2011

Related U.S. Application Data

(60) Provisional application No. 61/139,988, filed on Dec. 22, 2008.

(51) Int. Cl.
*G01N 33/554* (2006.01)
*G01N 33/53* (2006.01)

(52) U.S. Cl.
USPC .............................. 435/7.32; 435/7.2; 435/7.1

(58) Field of Classification Search
None
See application file for complete search history.

(56) References Cited

U.S. PATENT DOCUMENTS

| | | | |
|---|---|---|---|
| 2008/0193966 A1 | 8/2008 | Steiner et al. | |
| 2009/0010944 A1* | 1/2009 | Moe et al. | 424/174.1 |
| 2010/0240075 A1* | 9/2010 | Granoff et al. | 435/7.32 |

OTHER PUBLICATIONS

Morley et al. Pediatr. Infect. Dis. J. 20: 1054-1061, 2001.*
Toppero et al. JAMA 281: 1520-1527, 1999.*
Welsch et al. J. Immunology 172: 5606-5615, 2004.*
Welsch & Granoff (2007) "Immunity to *Neisseria meningitidis* Group B in Adults despite Lack of Serum Bactericidal Antibody" *Clin. Vaccine Immunol.* 14(12):1596-1602.
Aase, et al. (1995) "Comparison among opsonic activity, antimeningococcal immunoglobulin G response, and serum bactericidal activity against meningococci in sera from vaccinees after immunization with a serogroup B outer membrane vesicle vaccine" *Infect. Immun.* 63(9): 3531-3536.
Aase, et al. (1998) "Opsonophagocytic and bactericidal activity mediated by purified IgG subclass antibodies after vaccination with the Norwegian group B meningococcal vaccine" *Scand. J. Immunol.* 47(4):388-396.
Amir, et al. (2005) "Naturally-acquired immunity to *Neisseria meningitidis* group A" *Vaccine* 23(8):977-983.
Andrews, et al. (2003) "Validation of serological correlate of protection for meningococcal C conjugate vaccine by using efficacy estimates from postlicensure surveillance in England" *Clin Diagn Lab Immunol* 10(5):780-786.
Balmer & Borrow (2004) "Serologic correlates of protection for evaluating the response to meningococcal vaccines"*Expert Rev Vaccines* 3(1):77-87.
Borrow, et al. (2001) "Serological basis for use of meningococcal serogroup C conjugate vaccines in the United Kingdom: reevaluation of correlates of protection" *Infect Immun* 69(3):1568-1573.
Borrow, et al. (2005) "Meningococcal surrogates of protection—serum bactericidal antibody activity" *Vaccine* 23(17-18):2222-2227.
Borrow, et al. (2006) "*Neisseria meningitidis* group B correlates of protection and assay standardization—international meeting report Emory University, Atlanta, Georgia, United States, Mar. 16-17, 2005" *Vaccine* 24(24):5093-5107.
Findlow, et al. (2006) "Comparison and correlation of *Neisseria meningitidis* serogroup B immunologic assay results and human antibody responses following three doses of the Norwegian meningococcal outer membrane vesicle vaccine MenBvac" *Infect. Immun.* 74(8):4557-4565.
Goldschneider, et al. (1969) "Human immunity to the meningococcus. I. The role of humoral antibodies" *J. Exp. Med.* 129(6):1307-1326.
Goldschneider, et al. (1969) "Human immunity to the meningococcus. I. Development of natural immunity" *J Exp Med* 129(6):1327-1348.
Granoff, et al. (2005) "Persistence of group C anticapsular antibodies two to three years after immunization with an investigational quadrivalent *Neisseria meningitidis*-diphtheria toxoid conjugate vaccine" *Pediatr. Infect. Dis. J.* 24(2):132-136.
Guttormsen, et al. (1993) "Cross-reacting serum opsonins to meningococci after vaccination" *J. Infect. Dis.* 167(6):1314-1319.
Halstensen, et al. (1991) "Serum opsonins to serogroup B meningococci after disease and vaccination" *NIPH Ann.* 14(2):157-65; discussion 166-7.
Ison, et al. (1995) "Whole blood model of meningococcal bacteraemia—a method for exploring host-bacterial interactions" *Microb. Pathog.* 18(2):97-107.
Ison, et al. (1999) "Assessment of immune response to meningococcal disease: comparison of a whole-blood assay and the serum bactericidal assay" *Microb. Pathog.* 27(4):207-214.

(Continued)

*Primary Examiner* — S. Devi
(74) *Attorney, Agent, or Firm* — Carol L. Francis; Bozicevic, Field & Francis LLP

(57) ABSTRACT

The present disclosure provides methods for assessing bactericidal antibodies in a biological sample by use of human fresh whole blood from a non-immune human as a reaction medium for the assay.

12 Claims, 7 Drawing Sheets

(56) References Cited

OTHER PUBLICATIONS

Ison, et al. (2003) "Age dependence of in vitro survival of meningococci in whole blood during childhood" *Pediatr. Infect. Dis. J.* 22(10): 868-873.

Jodar, et al. (2000) "Standardisation and validation of serological assays for the evaluation of immune responses to *Neisseria meningitidis* serogroup A and C vaccines" *Biologicals* 28(3):193-197.

Jones, et al. (2000) "Lack of immunity in university students before an outbreak of serogroup C meningococcal infection" *J. Infect. Dis.* 181(3):1172-1175.

Lehmann, et al. (1991) "Immunization against serogroup B meningococci. Opsonin response in vaccinees as measured by chemiluminescence" *APMIS* 99(7-12):769-772.

Lehmann, et al. (1999) "Human opsonins induced during meningococcal disease recognize transferrin binding protein complexes" *Infect. Immun.* 67(12):6526-6532.

Martinez, et al. (2002) "Opsonophagocytosis of fluorescent polystyrene beads coupled to *Neisseria meningitidis* serogroup A, C, Y, or W135 polysaccharide correlates with serum bactericidal activity" *Clin. Diagn. Lab. Immunol.* 9(2):485-488.

Maslanka, et al. (1997) "Standardization and a multilaboratory comparison of *Neisseria meningitidis* serogroup A and C serum bactericidal assays" *Clin Diagn Lab Immunol* 4(2):156-167.

Mitchell, et al. (1996) "Analysis of meningococcal serogroup C-specific antibody levels in British Columbian children and adolescents" *J. Infect. Dis.* 173(4):1009-1013.

Mountzouros & Howell (2000) "Detection of Complement Mediated Antibody-Dependent Bactericidal activity in a Fluorescence-Based Serum Bactericidal Assay for Group B *Neisseria meningitidis*" *J. Clin. Microbiol.* 38(8):2878-2884.

Næss, et al. (1999) "Human IgG subclass responses in relation to serum bactericidal and opsonic activities after immunization with three doses of the Norwegian serogroup B meningococcal outer membrane vesicle vaccine" *Vaccine* 17(7-8):754-764.

Ngampasutadol, et al. (2008) "Human factor H interacts selectively with *Neisseria gonorrhoeae* and results in species-specific complement evasion" *J. Immunol.* 180(5):3426-3435.

Plested, et al. (2001) "Functional opsonic activity of human serum antibodies to inner core lipopolysaccharide (galE) of serogroup B meningococci measured by flow cytometry" *Infect. Immun.* 69(5):3203-3213.

Plested, et al. (2008) "Vaccine-induced opsonophagocytic immunity to *Neisseria meningitidis* group B" *Clin. Vaccine Immunol.* 15(5):799-804.

Quakyi, et al. (1999) "Immunization with meningococcal outer-membrane protein vesicles containing lipooligosaccharide protects mice against lethal experimental group B *Neisseria meningitidis* infection and septic shock" *J. Infect. Dis.* 180(3):747-754.

Romero-Steiner, et al. (2006) "Use of opsonophagocytosis for serological evaluation of pneumococcal vaccines" *Clin. Vaccine Immunol.* 13(2):165-169.

Rosenqvist, et al. (1999) "Functional activities and epitope specificity of human and murine antibodies against the class 4 outer membrane protein (Rmp) of *Neisseria meningitidis*" *Infect. Immun.* 67(3):1267-1276.

Ross, et al. (1987) "Killing of *Neisseria meningitidis* by human neutrophils: implications for normal and complement-deficient individuals" *J. Infect. Dis.* 155(6):1266-1275.

Santos, et al. (2001) "Importance of complement source in measuring meningococcal bactericidal titers" *Clin. Diagn. Lab. Immunol.* 8(3):616-623.

Trotter, et al. (2007) "Seroprevalence of bactericidal and anti-outer membrane vesicle antibodies to *Neisseria meningitidis* group B in England" *Clin. Vaccine Immunol.* 14(7):863-868.

Welsch, et al. (2004) "Naturally acquired passive protective activity against *Neisseria meningitidis* Group C in the absence of serum bactericidal activity" *Infect. Immun.* 72(10):5903-5909.

Welsch, et al. (2008) "Complement-dependent synergistic bactericidal activity of antibodies against factor H-binding protein, a sparsely distributed meningococcal vaccine antigen" *J. Infect. Dis.* 197(7):1053-1061.

Zollinger, et al. (1983) "Importance of complement source in bactericidal activity of human antibody and murine monoclonal antibody to meningococcal group B polysaccharide" *Infect. Immun.* 40(1):257-264.

\* cited by examiner

Figure 3
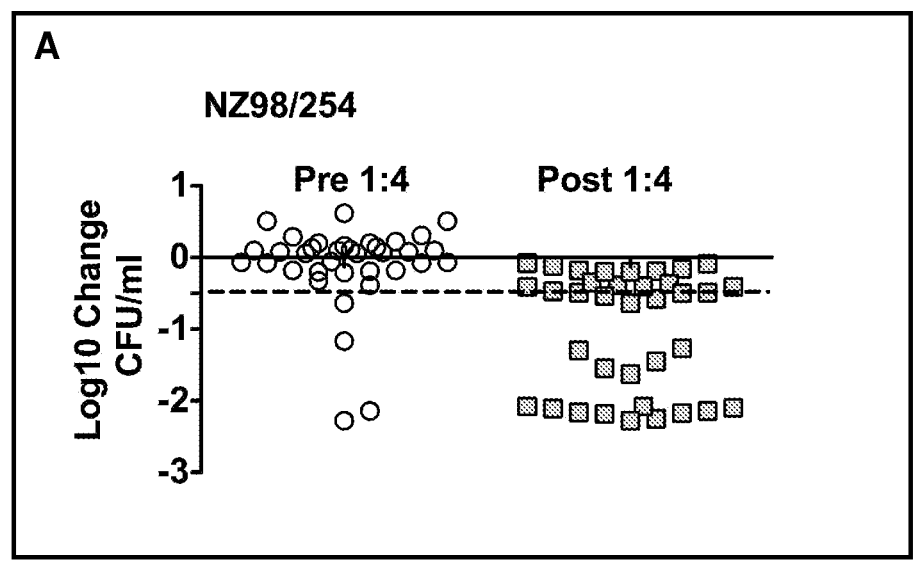
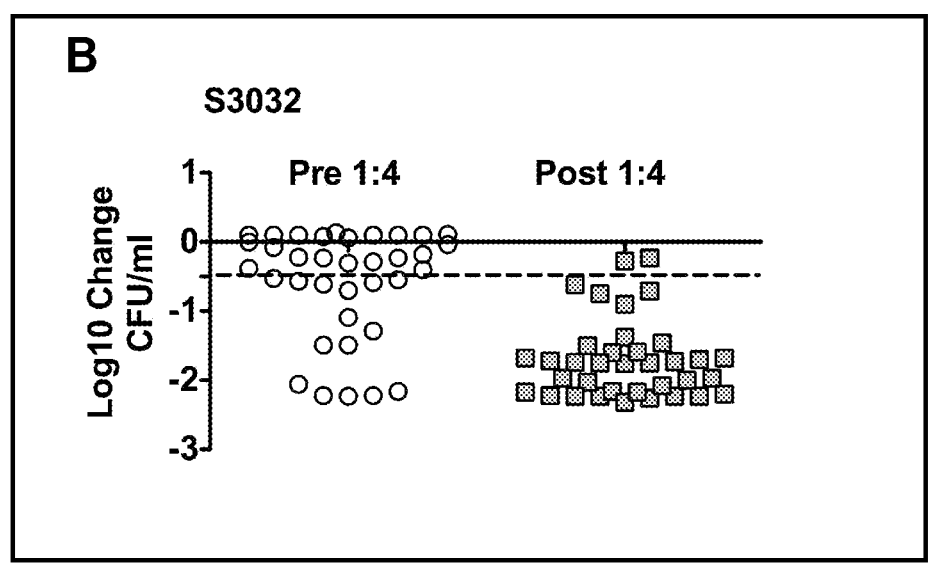

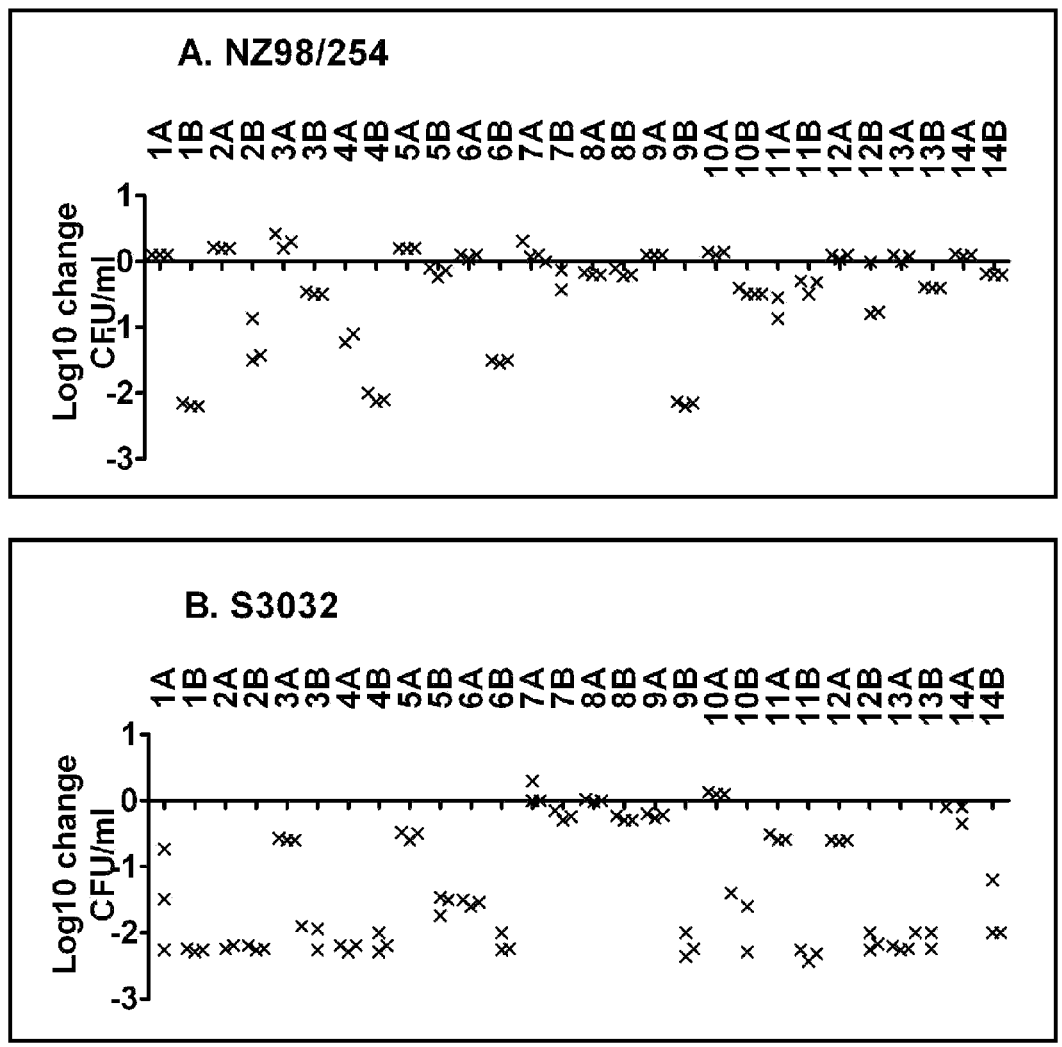

EX-VIVO PASSIVE PROTECTION BACTEREMIA ASSAY

CROSS REFERENCED TO RELATED APPLICATION

This application claims priority to U.S. Provisional Application No. 61/139,988 filed Dec. 22, 2008, which is incorporated herein by reference in its entirety and for all purposes.

GOVERNMENT SUPPORT

This work was supported by National Institutes of Health grant RO1 AI46464 from the National Institute of Allergy and Infectious Diseases, NIH. The federal government has certain rights in this invention.

TECHNICAL FIELD

This present disclosure relates to assays for bactericidal activity of antibodies against a bacterium.

BACKGROUND

*Neisseria meningitidis*, a commensal organism that is found frequently in the throat of healthy adolescents and which can invade the bloodstream and cause meningitis or rapidly fatal sepsis, is strictly a human pathogen. Reliable animal models of meningococcal disease have been difficult to develop. Many encapsulated strains of *N. meningitidis* that are highly pathogenic in humans are readily cleared from the bloodstream of commonly used experimental animals such as rabbits, mice and rats. Clearance may result in part from the role of the bacterial protein fH binding protein (fHbp), which binds human complement factor H (fH), a molecule that down-regulates complement activation. Binding of human fH to the bacterium increases resistance of the organism to complement-mediated bacterial killing and may be an important mechanism that enables *N. meningitidis* to circumvent innate host defenses. With *N. gonorrhoeae*, binding of fH is restricted to human fH, which may in part explain species-specific restriction of natural gonococcal infection (Ngampasutadol, J. et al. (2008) J Immunol 180:3426-3435).

Considerable data indicate that serum complement-mediated bactericidal antibody confers protection against meningococcal disease (Goldschneider, I. et al. (1969) J Exp Med 129:1307-1326; Goldschneider et al. (1969) J Exp Med 129: 1327-1348; Borrow, R. et al. (2005) Vaccine 23:2222-2227; Balmer, P. et al. (2004) Expert Rev Vaccines 3:77-87; Andrews, N et al. (2003) Clin Diagn Lab Immunol 10:780-786; Borrow, R. et al. (2001) Infect Immun 69:1568-1573). For example, in a seminal study Goldscheider et al. investigated the ability of serum complement-mediated bactericidal antibodies to confer protection against epidemic group C meningococcal disease in military recruits (Goldschneider et al. 1969, J Exp Med 129(6): 1307-26; Goldschneider et al. 1969, J Exp Med 129(6): 1327-48). Eighty-two percent of the more than 14,000 subjects had serum bactericidal titers of ≥1:4 against the epidemic strain but 51 of the 53 subjects who subsequently developed meningococcal disease had serum bactericidal titers <1:4. The authors concluded that a titer of ≥1:4 conferred protection against disease but also pointed out that many of the estimated 2600 recruits with titers <1:4 were likely exposed to the epidemic strain and did not develop disease. Indeed more than half of a small group of recruits with SBA titers <1:4 who were demonstrated to have acquired throat carriage of the group C epidemic strain did not develop disease. Therefore, while titers ≥1:4 conferred protection, titers <1:4 were not necessarily an indicator of susceptibility to disease.

A more recent study in the United Kingdom reported that the incidence of group B meningococcal disease declined between ages 1 and 10 years without a corresponding increase in the prevalence of group B serum bactericidal titers of ≥1:4 (Trotter et al. (2007) Clin Vaccine Immunol 14(7): 863-8). This study also found a lower prevalence of serum bactericidal activity titers in young adults (about 50%) than that reported in the Goldschneider study (about 80% to 90%). Other recent studies in North America or other countries in Europe confirm that SBA titers of ≥1:4 in adults are relatively uncommon (depending on the strain, typically 10 to 25% of adults) (Mitchell et al. 1996, J Infect Dis 173(4): 1009-13; Jones et al. 2000, J Infect Dis 181(3): 1172-5; Welsch and Granoff, 2004, Infect Immun 72(10): 5903-9; Amir et al. 2005, Vaccine 23(8): 977-83; Granoff et al. 2005, Pediatr Infect Dis J 24(2): 132-136). Thus, while SBA titers of ≥1:4 were prevalent in the 1960s, they are much less common now without a corresponding increase in the incidence of meningococcal disease (rates of disease in the U.S. since 2000 are the lowest in the last 50 years). Collectively, these seroepidemiologic data are inconsistent with the hypothesis that serum bactericidal titers of ≥1:4 are required for protection against meningococcal disease. Alternative hypotheses include protection by complement-mediated bactericidal antibodies present at serum dilutions <1:4, and/or the ability of opsonic activity to confer protection in the absence of SBA.

Several standardized protocols for group A and C bactericidal assays were developed that use infant rabbit serum as a complement source instead of human serum (Maslanka, S. E. et al. (1997) Clin Diagn Lab Immunol 4:156-167; Jodar, L. et al. (2000) Biologicals 28:193-197). Although rabbit complement was selected for these protocols because of greater ease of standardization, it has been known for many years that rabbit complement augments serum bactericidal titers as compared with titers measured with human complement (Zollinger, W. D. et al. (1983) Infect Immun 40:257-264; Santos, G. F. et al. (2001) Clin Diagn Lab Immunol 8:616-623). While serum bactericidal titers measured with rabbit complement have been correlated with the effectiveness of meningococcal vaccination introduced to large populations (Borrow, R. et al. (2005) Vaccine 23:2222-2227; Balmer, P. et al. (2004) Expert Rev Vaccines 3:77-87; Andrews and Borrow (2003) Clin Diagn Lab Immunol 10:780-786), many of these sera would lack bactericidal activity if tested with human complement. Thus, the correlations observed with rabbit complement may not accurately or totally reflect the actual mechanisms by which the vaccine-induced antibodies conferred protection.

A whole blood bactericidal assay (WBA) was used to measure naturally-acquired immunity (Ison et al. (2003) Pediatr Infect Dis J 22(10): 868-73; Ison et al. (1995) Microb Pathog 18(2): 97-107), or antibody responses of children (Ison et al. (1999) Microb Pathog 27(4): 207-14) and adults (Findlow et al. (2006) Infect Immun 74(8): 4557-65) to meningococcal vaccination. This assay used fresh blood samples obtained before and after immunization from each immunized subject. As pointed out by Findlow et al (2006), WBA is not practical for measurement of responses to vaccines since fresh blood is required of each assay, and the assay described cannot be performed on stored blood or serum samples. Thus, use of fresh whole blood samples from clinical trial subjects or from patients to assess bactericidal antibodies raised in response to a vaccine is impractical or impossible. For example, comparison of pre-immune bactericidal antibodies in fresh whole blood of a subject and post-immune bactericidal antibodies in fresh whole blood of the same subject and under the same assay conditions is simply not possible—the pre-immune blood is no longer "fresh" by the time the post-immune sample is available. Further, when independent assays are performed on two samples on different days, there is less precision in determining whether the respective titers are different than when the samples are assayed simultaneously.

Opsonic activity has also been used to assess protective antibodies to *N. meningitidis* that might be undetected by serum bactericidal activity assays (Ross et al. 1987, J Infect Dis 155(6): 1266-75; Halstensen et al. 1991, NIPH Ann 14(2): 157-65; discussion 166-7; Lehmann et al. 1991, Apmis 99(8): 769-72; Guttormsen et al. 1993, J Infect Dis 167(6): 1314-9; Aase et al. 1995, Infect Immun 63(9): 3531-6; Aase et al. 1998, Scand J Immunol 47(4): 388-96; Lehmann et al. 1999, Infect Immun 67(12): 6526-32; Naess et al. 1999, Vaccine 17(7-8): 754-64; Quakyi et al. 1999, J Infect Dis 180(3): 747-54; Rosenqvist et al. 1999, Infect Immun 67(3): 1267-76; Plested et al. 2001, Infect Immun 69(5): 3203-13; Martinez et al. 2002, Clin Diagn Lab Immunol 9(2): 485-8; Borrow et al. 2006, Vaccine 24(24): 5093-107; Romero-Steiner et al. 2006, Clin Vaccine Immunol 13(2): 165-9; Plested et al. (2008) Clin Vaccine Immunol 15(5): 799-804). This assay typically assays test sera that has been heated to remove internal complement activity, to which exogenous rabbit or human serum is added as a complement source, and fractionated or unfractionated peripheral blood mononuclear leukocytes or a monocytic cell line grown in tissue culture are added as the phagocytic effector cells. Because paired pre- and post-immunization sera from an individual, or groups of sera from persons given different vaccines, can be assayed together in one OPA assay, the ability to determine changes in titer after vaccination, or differences in vaccine response between groups, is greater with the OPA than with the WBA described above. However, OPA assays are typically done in reaction mixtures containing diluted non-immune serum as a complement source (typically 5%, 10% or 20%). The results therefore may be less sensitive for detecting OPA bactericidal activity than with the WBA.

SUMMARY

The present disclosure provides methods for assessing bactericidal antibodies in a biological sample by use of human fresh whole blood from a non-immune human as a reaction medium for the assay. In certain embodiments, the method for detection of bactericidal antibodies in a biological sample comprises combining in a reaction mixture: a biological sample suspected of containing bactericidal antibodies, a viable Gram-negative pathogenic bacterium of interest, and fresh human whole blood obtained from a non-immune human donor which does not contain detectable bactericidal antibodies effective against the pathogenic bacterium of interest, wherein the human from which the human biological sample was obtained is not the non-immune human donor, and wherein the fresh human whole blood contains an anticoagulant that does not significantly affect complement activation or complement activity, and detecting the presence or absence of bactericidal antibodies in the sample by assessing viability of the Gram negative bacterium, wherein decreased viability of the Gram negative bacterium in the presence of the biological sample indicates the sample contains bactericidal anti-bacterial antibodies. In certain cases, the biological sample is human serum. In particular examples, the biological sample is human plasma. In some cases, the biological sample is a supernatant of an antibody secreting cell. In other embodiments, the biological sample is mouse serum. In particular embodiments, the biological sample in the reaction mixture is a pre-immune biological sample and the method further comprises combining in a separate reaction mixture: a biological post-immune sample suspected of containing bactericidal antibodies, wherein the post-immune sample and the pre-immune sample are obtained from the same subject and wherein the post-immune sample is obtained after administration of an immunogenic composition to the subject; a viable Gram negative bacterium of interest; and fresh human whole blood which does not contain detectable bactericidal antibodies effective against a bacterium of interest, wherein the fresh human whole blood is obtained from a non-immune human donor, wherein the human from which the human biological sample was obtained is not the non-immune human donor, and wherein the fresh human whole blood contains an anticoagulant that does not significantly affect complement activation or complement activity; and the detecting comprising detecting the presence or absence of bactericidal antibodies in the pre-immune sample and in the post-immune sample by assessing viability of the bacterium in the samples, wherein the presence or absence of bactericidal antibodies in the post-immune sample as compared to the pre-immune sample is indicative of the ability of an immunogenic composition administered to the subject to elicit antibodies that are bactericidal for the Gram negative bacterium. In exemplary embodiments, the Gram negative bacterium is a *Neisseria* bacterium and the immunogenic composition comprises an antigen intended to elicit anti-Neisserial antibodies. In particular examples, the *Neisseria* bacterium is *Neisseria meningitidis*. In certain embodiments, the pre-immune sample and the post-immune samples are a pre-immune serum sample and a post-immune serum sample, respectively. In some cases, the pre-immune serum sample and a post-immune serum sample are heat-inactivated prior to the combining. In some examples, the subject is a human. Alternatively, the subject is a mouse.

A method of screening for a candidate vaccine is also provided. The method comprise combining in a first reaction mixture: a pre-immune biological sample obtained from a subject prior to administration of a candidate vaccine comprising an immunogenic composition; a viable Gram-negative bacterium; and fresh human whole blood, which does not contain detectable bactericidal antibodies effective against a bacterium of interest, wherein the fresh human whole blood is obtained from a non-immune human donor, wherein the human from which the human pre-immune sample is obtained is not the subject to whom the candidate vaccine is to be administered, and wherein the fresh human whole blood contains an anticoagulant that does not significantly affect complement activation or complement activity; combining in a second reaction mixture: a post-immune sample obtained from the subject following administration of the candidate vaccine; the fresh human whole blood; and the viable Gram negative bacterium; and detecting the presence or absence of bactericidal anti-bacterial antibodies in each of the pre-immune and post-immune samples by assessing viability of the bacterium. In certain cases, the pre-immune and post-immune samples are human serum samples. In exemplary embodiments, the Gram negative bacterium is *Neisseria* bacterium. In same embodiments, the *Neisseria* bacterium is *Neisseria meningitidis*.

A reaction mixture comprising a biological sample suspected of containing bactericidal antibodies; a viable Gram negative bacterium of interest; and fresh human whole blood which does not contain detectable bactericidal antibodies effective against the bacterium of interest, wherein the fresh human whole blood is obtained from a non-immune human donor, wherein the human from which the human biological sample was obtained is not the non-immune human donor, and wherein the fresh human whole blood contains an anticoagulant that does not significantly affect complement activation or complement activity is provided.

BRIEF DESCRIPTION OF THE DRAWINGS

FIG. 1, Panel B shows the corresponding OPA titers ≥1:4 for the two strains tested, NZ98/254 and S3032, which were relatively resistant to SBA by the sera from the immunized persons.

Figure 1:
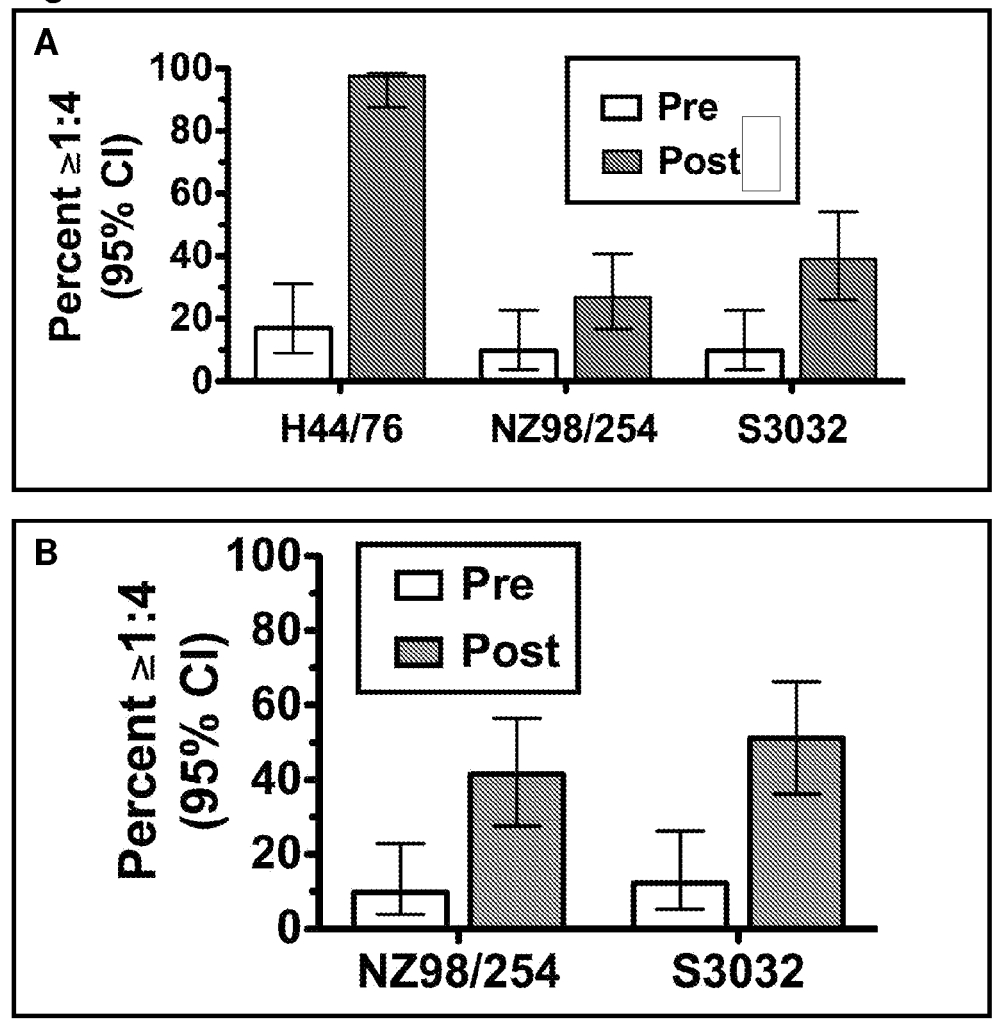
FIG. 1, Panel A shows results of complement-mediated serum bactericidal assay and of sera obtained from 36 healthy adults immunized with 3 doses of a 3-component (five antigen) investigational recombinant protein vaccine adsorbed with aluminum hydroxide (Giuliani et al, PNAS 2006).

FIG. 3 shows results of ex-vivo passive protection bactericidal assay (PPA) carried out using whole blood from a non-immune donor, and stored pre-immunization and post-immunization sera (same set of 36 sera as used for FIG. 1), and strain NZ98/254 (panel A) and strain S3032 (panel B).

FIG. 4 shows the reproducibility of the ex-vivo passive protection bactericidal assay (PPA) on pre- and post-immunization sera from 14 subjects on strains NZ98/254 (Panel A) and S3032 (Panel B). Sera labeled 1A, 2A, 3A, etc, present pre-immunization sera. Sera labeled 1B, 2B, 3B, represent the respective post-immunization sera. Each "X" represents the results of an independent assay (three assays done on each sample).

FIG. 5A shows results from PPA assay on sera with SBA titers <1:4 and sera with SBA titers ≥1:4 using strain NZ98/254. For each serum, the three data points are the results of three independent assays performed on different days.

FIG. 5B shows results from PPA assay on sera with SBA titers <1:4 and sera with SBA titers ≥1:4 using strain S3032 as described in the legend for FIG. 5A.

FIG. 6 shows a comparison of the respective results from sera tested with SBA, OPA and PPA.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent such publications may set out definitions of a term that conflicts with the explicit or implicit definition of the present disclosure, the definition of the present disclosure controls.

It must be noted that as used herein and in the appended claims, the singular forms "a", "an", and "the" include plural referents unless the context clearly dictates otherwise. Thus, for example, reference to "a sample" includes a plurality of samples and reference to "the bacterium" includes reference to one or more bacteria, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

The present disclosure provides methods for assessing bactericidal antibodies in a human serum sample by use of human fresh whole blood as a reaction medium for the assay.

Definitions

"Bactericidal antibody" as used herein refers to an antibody that facilitates complement-mediated killing of a bacterium.

The term "protective immunity" means that a vaccine or immunization schedule that is administered to a mammal induces an immune response that prevents, retards the development of, or reduces the severity of a disease that is caused by a pathogenic bacteria, such as, *Neisseria meningitidis*, or diminishes or altogether eliminates the symptoms of the disease. Protective immunity may be accompanied by production of bactericidal antibodies. It should be noted that production of bactericidal antibodies against *Neisseria meningitidis* is accepted in the field as predictive of a vaccine's protective effect in humans. (Goldschneider et al., 1969, J. Exp. Med. 129:1307; Borrow et al. 2001 Infect Immun. 69:1568).

"Ex-vivo" refers to refers to experimentation or measurements done in or on living tissue in an artificial environment outside the host with the minimum alteration of the natural conditions.

"Pre-immunization sample" or "pre-exposure sample" refers to a sample obtained from a subject before the subject is knowingly exposed to an antigen, for example, by administering the antigen to the subject.

"Post-immunization sample" or "post-exposure sample" refers to a sample obtained from a subject after the subject has been knowingly exposed to an antigen, for example, by administering the antigen to the subject.

"Complement" refers to a collection of serum proteins that provide for a functional complement cascade, which is the biochemical cascade that promotes bacterial death. As such, "complement" as used herein refers to a collection of serum proteins that can mediate a functional complement cascade associated with the classical pathway, the alternative pathway, or both, and may further include serum proteins that can mediate the mannose-binding lectin pathway.

Overview

The present disclosure provides an ex vivo model of bactericidal activity for detection of bactericidal antibodies in a sample by using fresh whole blood from a non-immune human donor. Thus the present disclosure provides a system that uses fully human blood components to assess bactericidal activity of antibodies in a sample. These assays may be used to detect bactericidal antibodies from any source, e.g., in heat-inactivated serum samples. Of particular interest is the application of this assay to examine the presence or absence of bactericidal antibodies in pre-immunization sera and post-immunization sera in parallel assays. This assay also allows simultaneous comparison of titers of bactericidal anti-bacteria antibodies elicited from immunization using different vaccines by providing a controlled background as all of the assays may be performed using blood from a single donor. Stated differently, the assays of the present disclosure allow for assaying a plurality of samples in parallel in the same reaction mixture milieu and provide an ex vivo model of bactericidal activity mediated by the human complement system and other human blood components. Because the assays of the present disclosure thus can be used to provide information about the ability of a sample to clear the bacteria from blood by either complement-mediated bactericidal activity, opsonophagocytic bactericidal activity, or a combination of the two mechanisms, the whole blood PPA assays are thus sometimes referred to herein as an "ex vivo passive protection assay". The subject assay utilizes fresh whole blood from a non-immune human donor, where the blood is modified by using an anticoagulant that does not significantly affect complement activation or complement activity. Exemplary anticoagulants of this type include specific thrombin inhibitors, such as lepirudin.

Although the present disclosure discusses assays for use in detecting anti-Neisserial bactericidal antibodies, the methods provided herein may be used to detect bactericidal antibodies directed to any Gram-negative pathogenic bacterium of interest that are killed by antibodies and complement and/or phagocytic cells. The bacterium may infect humans, livestock (e.g., cattle, hogs, poultry, or fish, etc.). Exemplary target bacterium includes *Neisseria, Pseudomonas, Shigella, Campylobacter, Salmonella, Hemophilus, Borellia*, etc. Of particular interest are pathogenic bacteria for which detection of a threshold level of bactericidal antibodies is indicative of a protective humoral immune response in the subject from whom the sample was obtained.

Assays For Detection of Bactericidal Anti-*Neisseria* Antibodies

In certain embodiments, the present disclosure provides methods and compositions for the detection of bactericidal anti-*Neisseria* antibodies in a sample.

Fresh Human Whole Blood From Non-Immune Donor

The assay of the present disclosure uses fresh whole blood from a human, non-immune donor. "Fresh blood" as used in the context of "fresh whole human blood" means blood that usually has not been stored for more than about 6 hours, usually not more than about 4hours after being obtained from a subject. Usually fresh blood is maintained such that it exhibits at least about 90% of its original hemolytic complement activity. Fresh blood can be stored at 18° C. to 26° C. until time of use in the assay. In exemplary embodiments, fresh blood is stored at ambient (room) temperature.

"Fresh blood" encompasses blood samples modified in a manner compatible for use in the assays described herein (e.g., addition of anti-coagulants, or depletion of IgG, for example by incubation with beads conjugated with Protein A or Protein G, etc.).

As noted above, fresh human blood for use in the assay is obtained from a non-immune human donor. "Non-immune" with reference to a donor refers to a subject that does not have any detectable bactericidal antibodies against a particular bacterium of interest, where the bacterium of interest is determined by the target bacterium (bacteria) for bactericidal antibodies to be assayed in a test sample and using whole blood from the non-immune donor as described herein. "Non-immune donor" encompasses "naïve donors", where a "naïve" donor is one that is known not to have been exposed to the bacteria to be assayed. In general, a "non-immune donor" is a donor whose blood supports no significant killing (less than 10% decrease in CFU/ml) over a 90 min to 4 hour incubation period when the target bacterial strain is cultured at 37° C. In certain cases, the blood from a "non-immune donor" supports a 2 log 10 increase, 1 log 10 increase, or a 0.5 log 10 increase in CFU/ml blood during the 90 min to 4 hr incubation period in whole blood assay.

A non-immune donor is generally identified by obtaining a sample of blood from the donor and assaying the sample for the presence of bactericidal antibodies that are directed against a bacteria of interest, e.g., *Neisseria*, a particular strain(s) of *Neisseria* (e.g., which are the target of a vaccine), and the like. When, for example, where a vaccine is to be tested for eliciting bactericidal antibodies against strain A, blood sample from a non-immune donor is tested for the presence or absence of detectable bactericidal antibodies against strain A. A sample that is known to contain bactericidal antibodies against strain A may be used as a positive control. In general, blood from a non-immune donor allows for survival or growth of a bacterium of interest because of the absence of detectable or significant bactericidal antibodies against that bacterium.

The donor sample can be assayed using a whole blood assay, serum bactericidal assay, opsonophagocytic assay, or a combination of these assays or other assays known in the art for detection of bactericidal antibodies. In general, a whole blood assay is used to detect the presence or absence of bactericidal antibodies in whole blood of a candidate non-immune donor.

In certain embodiments, non-immune donors that yield similar respective results with different test samples may be identified. Thus, blood from different individual non-immune donors may be used to compare test samples. For example, in the comparison of a pre- and post-immunization sample from subject A to a pre- and post-immunization sample from subject B by the passive protection assay, blood from a first non-immune donor may be used to assay subject A's sample and blood from a second non-immune donor may be used to assay subject B's sample.

Samples

Any sample suspected of containing bactericidal antibodies (e.g., bactericidal anti-*Neisseria* antibodies) may be assayed, for example a biological sample, e.g., obtained from a subject (e.g., blood or blood fraction (e.g., serum), mucosal secretion, and the like), from cell culture (e.g., from supernatant of an antibody-secreting cell (e.g., hybridoma)). Serum samples suspected of containing bactericidal antibodies are of particular interest. In exemplary embodiments, the sample may be from an animal that has been immunized with a vaccine. For example, a mouse, rabbit, non-human primate, etc. The sample can be from a subject of interest, with humans being of particular interest.

Typically, where the sample may contain complement (e.g., as in a serum sample), the sample is treated to inactivate endogenous complement, e.g., by heating (e.g., at 56° C. for about 30 minutes). Different volumes (for example, 100 µl, 25 µl, 10 µg or 5 µl) of undiluted sera are added to a fixed volume of whole blood to achieve final dilutions of the test sera of 1:4, 1:8 or 1:16 in the reaction vial. The sample (e.g., a serum sample) also may be diluted in a buffer, e.g. Dulbecco's buffer, and a fixed volume of the diluted test serum is added to a fixed volume of blood so that the sample is assayed as serial dilutions to facilitate assessment of antibody titer. Samples to be tested for the presence or absence of bactericidal antibodies can be fresh or frozen prior to use. Where samples are assessed to determine effectiveness of a vaccine to elicit bactericidal antibodies (e.g., bactericidal anti-*Neisseria* antibodies), the samples can be obtained prior to and after immunization of a subject, referred to as "pre-immune" and "post-immune" samples. Such samples can be run in parallel so as to provide for assays of these pre- and post-immune samples under the same conditions, e.g., in the same fresh whole blood from the same donor.

Target Bacteria

The assay of the present disclosure can be used to assess bactericidal antibodies for any Gram-negative pathogenic bacteria of interest. The assays finds particular use in assessing bactericidal antibodies in serum where such bactericidal antibodies are accepted in the field as being indicative of a protective immune response in the human subject from which the serum sample was obtained. *Neisseria* are of particular interest.

For example, where the target bacteria is *Neisseria*, any suitable *Neisseria*, particularly a *Neisseria* bacteria expressing a surface fHbp, can be used as the target bacterium for detection of bactericidal antibodies in the assays described herein. Such *Neisseria* bacteria include *Neisseria meningitidis* and *N. gonorrhea*. The target bacterium can be selected in accordance with the specificity of the bactericidal antibodies to be assayed. For example, where the assay is to provide for detection of bactericidal anti-*Neisseria meningitidis* antibodies, the target bacterium can be any suitable *Neisseria meningitidis*, e.g., Group A, B, C, or W-135 *Neisseria meningitidis* or *Neisseria meningitidis* of any other capsular group of interest, a *Neisseria meningitidis* strain expressing a particular antigen of interest (e.g., v.1, v.2, or v.3 fHbp, including fHbp subvariants; PorA type, and the like). The assay can be used in connection with *Neisseria* genetically modified to express an antigen of interest. For example, the target bacterium can be selected to facilitate analysis of production of bactericidal anti-Neisserial antibodies following immunization with a vaccine.

Prior to use in the assay, the target bacteria may be cultured by methods known in the art, for example, in broth (e.g., Mueller-Hinton broth) or on an agar plate (e.g., chocolate agar plates). Preferably bacteria grown to early- or mid-log phase are used for the assay. If cultured on an agar plate, the bacteria is removed from the agar plate and resuspended. If cultured in liquid broth, the bacteria can be centrifuged and resuspended. In general, the bacteria are provided to a desired cell number, and can be provided in samples of differing cell numbers as a control. For example, bacteria can be resuspended at a cell density of about $10^5$ to $10^8$ colony forming units (CFU)/ml, usually about $5 \times 10^7$ CFU/ml. The resuspension solution can be selected so as to be compatible for use with the detection assay, e.g., a buffer, typically HBSS (Hanks Basic Salt Solution) or phosphate buffered saline (PBS) supplemented with $MgCl_2$ and $CaCl_2$ and containing a protein such as bovine serum albumin (BSA).

Prior to use in the assay, the bacteria may be washed one or more times to remove components of culture broth. For example, the bacteria may be washed in buffer (e.g., containing BSA) and/or in heat-inactivated serum (e.g., depleted for IgG, e.g., so as to contain no detectable IgG). Washing generally involves resuspending the bacteria in a solution, pelleting the bacterial cells by centrifugation, and resuspending the bacteria, e.g., in reaction mixture buffer for use in the assay.

Reaction Mixtures

Reaction mixtures of the assays are prepared by combining, in any suitable order, assay reagents (e.g., fresh whole blood with an anticoagulant), a test serum and a *Neisseria* bacterium. The reaction mixture can be produced by combining these components in any suitable vessel, such as a test tube, the well of a microtiter plate, or a capillary tube. The components of the reaction mixture should be mixed thoroughly, which can be accomplished by any suitable method (e.g., by agitation). In general, the assay is performed with undiluted heat-inactivated test serum, undiluted blood and as small a volume as possible of physiologically compatible buffer containing the bacterial suspension to achieve the desired CFU/ml. The goal is to create conditions that mimic as closely as possible the respective concentrations of serum and blood cells that are present in whole blood. Reaction volumes of the reaction mixture can vary, and are usually on the order of microliters to milliliters (e.g. 50 µl, 100 µl, 500 µl, 1 ml, and the like). For example, the assay can be performed using fresh whole blood from a donor and test samples, where the total volume of both the blood and the test sample is in the microliter ranges, such as, about 25 µl, 50 µl, 75 µl, 100 µl, 500 µl or 1000 µl, etc. In certain embodiments the assay may be performed in microtiter plates. In certain embodiments, the assay may be partially or completely automated. The test samples can be provided in different dilutions in the reaction mixture, e.g., 1:2, 1:4, 1:5, 1:6, 1:8, 1:10, 1:12, 1:14, 1:16, 1:18, 1:20, 1:22, 1:24, or greater and the like with dilutions of 1:64 and greater being of interest.

The reaction mixture is incubated under conditions suitable for complement-mediated bactericidal antibody activity. For example, the reaction mixture can be incubated for a time sufficient to allow for complement-mediated bactericidal antibody activity (e.g., from about 15 min to 90 min, about 30 min to 90 min, and the like) and at a suitable temperature (e.g., ambient temperature or physiologically relevant temperature (e.g., about 37° C.)). In addition to test samples, control samples can be provided. Such control samples can include negative control samples (e.g., samples that parallel the conditions of test samples, but to which no biological sample is added, or to which an antibody having no detectable bactericidal activity is added, etc.) and/or positive controls (e.g., samples that parallel the conditions of test samples, but to which an antibody having known bactericidal activity for the target bacterium is added).

The reaction mixtures can contain additional components that are compatible with the assay as described herein. For example, an anti-coagulant that does not interfere with complement function may be added to the fresh whole blood from a non-immune donor. A number of such anticoagulants are known in the art, such as herudin (e.g., recombinant herudine), lepirudin, and variants thereof known in the art (e.g., variants in which the naturally-occurring amino acids have been deleted, added or substituted). Thus, in certain embodiments, the passive protection assay described herein uses an anti-coagulant that does not significantly affect complement activation or complement activity, i.e., does not significantly inhibit or activate complement activation or complement activity. Anticoagulants such as heparin or ethylene diamine tetraacetic acid affect complement activation or complement activity. For example, heparin binds to a variety of complement proteins and thereby affects both the classical and alternate amplification pathways. Heparin inhibits a portion of the complement cascade by inhibiting generation of the cell bound amplification pathway C3 convertases. It also acts as a complement inhibitor by interfering with the binding site on C3b for B. Furthermore, it prevents the consumption of B by D in the presence of C3b again indicating a direct action on C3b. Thus, in preferred embodiments an anti-coagulant, such as heparin, EDTA, which activates or interferes with complement activation or complement activity, may not be used.

The assay can be conducted by combining fresh whole blood from a non-immune donor with a pre-immunization sample from a subject and the target bacterium and in parallel, in a separate sample receiving area (e.g., a separate well of a microtiter plate or separate container), fresh whole blood from the same non-immune donor is mixed with a post-immunization sample from the same subject and the target bacterium. "Parallel" as used in the context of such assays is meant to encompass both preparation and assaying of such reaction mixtures at the same time, as well as within a period during which the whole blood from the non-immune donor is still fresh, e.g., the preparation of a first reaction mixture can precede the preparation of the second mixture by about an hour, 2 hours, 4 hours, up to 6 hours.

The assays of the present disclosure find use in assaying stored samples obtained from a vaccine trial. These samples may be obtained at different time points during the trial, for example, before the administration of the first dose of the vaccine, one month, two months or three months after the administration of the first dose, before and/or after a second dose, etc. These samples may be serum samples that have been heat inactivated to inactivate complement in the sample. Such samples may be a blood fraction sample (e.g., serum or plasma) that has been stored under conditions to preserve any bactericidal antibodies, if present (e.g., frozen or lyophilized).

Assays disclosed herein using fresh whole blood from a non-immune donor find use in assaying samples obtained from a plurality of vaccine trials. Use of whole blood from a single non-immune donor provides for a constant background for comparing the effectiveness of one vaccine to another vaccine.

Detection

Following incubation with test sample, the presence or absence of bactericidal anti-Neisserial antibodies is detected by assessing the viability of *Neisseria* in the reaction mixtures. This can be accomplished by, for example, plating the reaction mixture on a suitable medium (e.g., agar plates) and assessing colony forming units, culturing the reaction mixture in broth and assessing bacterial growth by cell density, FACS (see, e.g., Mountzouros et al., 2000, J. Clin. Microbiol. 38:2878-2884), and the like. The bactericidal titer is defined as the serum dilution at which a decrease in viable *Neisseria* is observed (e.g., a decrease in CFU per milliliter), typically a dilution resulting in a 50%, or 0.5 log 10 decrease, or 1.0 log 10 decrease (90% decrease) or 2.0 log 10 decrease (99% decrease) in viability as compared to a control. Results can also be described as serum dilution resulting in 50% decrease in survival compared to survival of negative control at time zero.

One of ordinary skilled in the art will appreciate the need for control reactions to be performed in parallel with the experimental reaction mixtures. For example, a sample containing known high, medium and low titers of bactericidal antibodies can be assayed as positive controls. In addition, a reaction mixture to which no sample has been added should be performed, as well as a reaction mixture to which serum from a non-immune subject has been added.

Vaccine Development

The assays disclosed herein can also be used to screen candidate vaccines for their ability to prevent or ameliorate infection by a bacterium. In general, a "vaccine" is an agent that, following administration, facilitates the host in mounting an immune response against the target pathogen. The humoral, cellular, or humoral/cellular immune response elicited can facilitate inhibition of infection by the pathogen against which the vaccine is developed. Of particular interest are prophylactic vaccines that elicit a protective immune response that inhibits infection by and/or replication of *Neisseria* bacteria, e.g., *Neisseria meningitidis, N. gonorrhea*, and the like. Also of interest are therapeutic vaccines which provide protection against challenge, e.g., by production of bactericidal anti-Neisserial antibodies.

Screening of a candidate vaccine can be accomplished by, for example, collecting pre-immunization sample from the subjects, administering the candidate vaccine, and collecting post-immunization sample from the subjects. The candidate vaccine can be administered by a single bolus (e.g., intraperitoneal or intramuscular injection, an oral dose), which can be optionally followed by one or more booster immunizations. The induction of an immune response can be assessed by examining antibody responses, e.g., using conventional assays and the assays described herein. The ex-vivo passive protection bactericidal assay described herein may used be to measure bactericidal anti-bacteria antibody titers in the pre-immunization samples and the post-immunization samples simultaneously for a plurality of candidate vaccines. Since, this assay may be performed using small volumes (in the microliter range) of fresh blood, a single donor may be used as a source of whole blood for the entire screen. Using a single donor can provide for improved reproducibility of this assay and provides a constant background. Further, because the assay can be conducted using only small volumes, only a relatively small volume of fresh whole blood from a single non-immune donor (e.g., 0.2 ml, 1 ml, 10 ml, 50 ml, 100 ml, etc.) can be used to conduct multiple assays in parallel.

EXAMPLES

The following example is provided to further illustrate the advantages and features of the present invention, but is not intended to limit the scope of the invention. While they are typical of those that might be used, other procedures, methodologies, or techniques known to those skilled in the art may alternatively be used.

Materials and Methods

Serum samples. Stored serum samples were provided by Novartis Vaccines from Phase 1 clinical trials with an investigational 3-component (five antigens) recombinant vaccine (GNA 2091, fHbp variant 1, GNA 2132, GNA 1030, and NadA) (Chiron Vaccines, Emeryville Calif. (now Novartis Vaccines, Cambridge, Mass.) (Giuliani, M. M. et al. 2006, Proc Natl Acad Sci USA 103(29): 10834-9). These sera came from 36 subjects, aged 18 to 50 years old. The dose of the vaccine was 60 μg per individual protein per dose (total=180 μg), which were adsorbed with aluminum hydroxide (total of 1.65 mg per injection). Subjects were given three doses, each separated by one-month intervals. Serum samples that had been obtained immediately before immunization (pre-immune sera) and at 1 month after the third dose were assayed (post third-immune sera). The sera were heated at 56° C. for 30 minutes to inactivate internal complement. The final serum dilution used in the SBA, OPA and PPA was 1:4.

Neisseria meningitidis strains. The three group B strains, H44/76-SL (B.15.P1.7,16, ST-32), NZ98/254 (B:4;P1.7-2,4 and ST 41/44 complex) and S3032 (B:19,7:P1.12,16, ST type, ST-6875) were used. The H44/76-SL strain was from an epidemic in Norway (Bjune et al. 1991, NIPH Ann 14(2): 125-30; Fredriksen, et al. 1991, NIPH Ann 14(2): 67-79). This strain H44/76-SL (seed lot) is referred to as H44/76. NZ98/254 (B:4;P1.7-2,4 and ST 41/44 complex) was a strain from a recent epidemic in New Zealand (Dyet and Martin, 2006, Epidemiol Infect 134(2): 377-83). S3032 (B:19,7: P1.12,16, ST type, ST-6875) was from a patient hospitalized in the U.S. (Frasch et al. 1985, Rev Infect Dis 7(4): 504-10. With respect to the three principal antigens in the vaccine, the H44/76 test strain was a high expresser of a fHbp in the variant 1 group with an identical amino acid sequence to fHbp in the vaccine while the NZ98/254 strain was a relatively low expresser of a subvariant of fHbp v.1 with a small number of amino acid differences from that of the vaccine (Welsch and Granoff, 2004, Infect Immun 72(10): 5903-9; Welsch et al. 2008, J Infect Dis 197(7): 1053-61). The third test strain, S3032, expressed a naturally-occurring chimeric of fHbp in the variant 2 and 3 groups (Genbank Accession number EU921901). All three strains had genes encoding GNA 2132. The GNA 2132 protein expressed by NZ98/254 and H44/76 strains had a homologous 63 amino acid peptide that was present in recombinant vaccine antigen while this segment was absent in GNA 2132 from strain S3032 (Welsch and Moe, 2003, J Infect Dis 188(11): 1730-40). Genbank accession numbers for GNA 2132 of NZ98/254, H44/76 and S3032 are AY315196, AF226436 and AY315192, respectively. None of the three strains had the gene for NadA.

Serum Bactericidal assay (SBA). This assay was performed as described elsewhere using early log-phase, broth grown N. meningitidis and human complement (Plested and Granoff, 2008, Clin Vaccine Immunol 15(5): 799-804; Welsch et al. 2008, J Infect Dis 197(7): 1053-61). The source of complement was non-immune serum from a healthy adult with normal total hemolytic complement activity and no detectable serum bactericidal antibodies against each of the test strains. Serum titers were assigned by interpolation of the dilution that gave 50 percent survival. Note that bacteria incubated with the negative control serum and complement typically showed a 150 to 250 percent increase in CFU/ml during the 60 minutes of incubation.

Opsonophagocytic killing assay (OPA). The OPA assay was performed using heat-inactivated test serum, log-phase, live bacteria (prepared in the same way as for the SBA), fresh purified human donor PMNs (three donors, heterologous FcγRIIA receptor, determined by PCR) and exogeneous human complement. The procedure was as described previously (Plested and Granoff, 2008, supra) except that C6-sufficient serum was used as a complement source instead of C6-depleted serum. A positive OPA titer was defined by a 50% decrease in CFU/ml after 1 hr incubation in the reaction mixture as compared with that of the negative controls at time zero (0).

Ex-vivo passive protection assay (PPA). Fresh blood from a healthy adult was obtained using a syringe containing recombinant hirudin (lepirudin, 27.8 μg/ml final concentration) as the anti-coagulant. The blood donor was the same person whose serum was used for complement to measure SBA and OPA. To each well of the microtiter plate, 65 μl of blood were added, 25 μl of test sera, and 10 μl of PBS buffer containing 15% heated-complement and 1% Bovine Serum Albumin, (Equitech) and approximately 4000 CFU. The positive controls were a relevant anti-PorA mAb (NIBSC, P1.4 or P1.12) and human serum samples with high, medium or low OPA and SBA against the respective test strains. Negative control sera were heat-inactivated serum from the complement donor or buffer alone. The microtiter plates were incubated for 90 mins at 37° C. in 5% CO2 with agitation on a MS 3 digital minishaker (IKA, Wilmington, N.C.) at 500 oscillations per min to completely mix the components. Samples were removed from the wells and quantitative cultures performed on chocolate agar plates, which were incubated at 37° C. in 5% CO2.

The following day CFU/ml was ascertained and the results were calculated as log 10 change in CFU/ml at 90 mins compared to that at time 0 with negative control test sera. Based on reproducibility of replicate assays performed on different days (see Results), we defined a positive PP activity as a serum giving≥0.5 log 10 decrease in CFU/ml, as compared to that at time 0 (i.e., about 70% decrease in CFU/ml). All assays were performed in duplicate and the results reported were from independent experiments performed on at least three occasions.

Example 1

Measurement of Bactericidal Activity of Stored Sera by SBA and OPA

Stored pre-immunization and post-immunization sera from 36 healthy adults immunized with three doses of a 3-component vaccine (five antigen vaccine, see materials and methods) were assayed by SBA and OPA. OPA was performed as described in (Plested and Granoff, 2008, Clin Vaccine Immunol 15(5): 799-804) except that C6-sufficient (i.e., non-depleted) complement was used instead of a C6-depleted complement. FIG. 1, Panel A shows proportions of subjects with protective SBA titers of ≥1:4 before and after immunization with the 3-component (five antigen) vaccine. Serum bactericidal activity against strains H44/76, NZ98/254 and S3032 were assayed. FIG. 1, Panel B shows proportions of subjects with protective OPA titers ≥1:4 before and after immunization with the 3-component (five antigen) vaccine. Opsonophagocytic activity against strains NZ98/254 and S3032 were assayed.

Example 2

Identification of a Non-Immune Individual

Blood from a healthy donor was tested for the presence of bactericidal anti-Neisserial antibodies against five strains: MC58, H44/76, 4243, NZ98/254 and S3032. This same donor was used as a source of serum for the SBA and OPA results shown in FIG. 1.

Figure 2A:
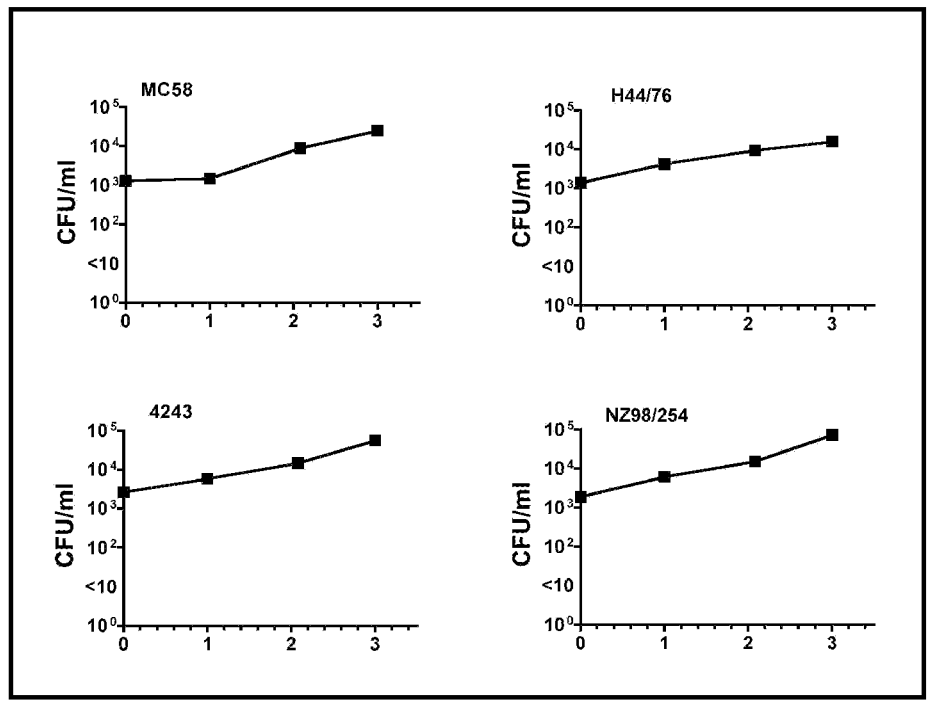
FIG. 2A shows survival and growth of four representative *N. meningitidis* strain (three group B and one group C) when incubated with whole blood assay from a healthy donor. The data show that the donor has no bactericidal anti-Neisserial antibodies to these strains. Therefore, blood from this donor is suitable for use as in ex vivo human meningococcal bacteremia model for testing passive protective activity of exogenous test antibodies or sera.

FIG. 2A shows the results of whole blood bactericidal assay (WBA) performed using fresh whole blood and strains MC58, H44/76, 4243, and NZ98/254. Recombinant hiruden was added as the anticoagulant. After the inoculation of the test strains, samples from the inoculated blood were taken at 0, 1, 2 and 3 hours and the colony forming units (CFU)/ml was determined. The growth of each of the strains in the whole blood indicated that the donor was non-immune or naive with respect to these strains as the donor lacked bactericidal antibodies for these strains. Depending on the strain tested, about 13 to 60% of donors were non-immune (Welsch and Granoff, 2007, Clin Vaccine Immunol 14: 1596-1602).

Figure 2B:
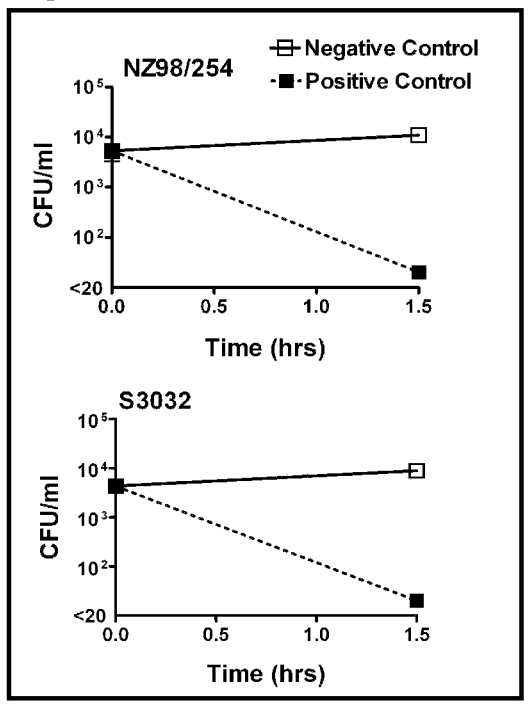
FIG. 2B shows results of the ex-vivo passive protection bactericidal assay (PPA) carried out using whole blood from the healthy non-immune donor to which has been added heat-inactivated sera from donors with SBA titers <1:4. The final dilution of the test sera was 1:4. One serum had no bactericidal activity in the PPA (negative control) while the other sera from a subject immunized with a Neisserial OMV vaccine had bacterial killing (positive control) in the PPA assay despite having a negative SBA titer.

FIG. 2B shows the results of an ex-vivo passive protection bacterimia assay (PPA) performed using fresh whole blood and strains NZ98/254 and S3032. Recombinant hiruden was added as the anticoagulant to the blood. One serum had no bactericidal activity in the PPA (negative control) while the other sera from a subject immunized with a Neisserial OMV vaccine had bacterial killing (positive control) in the PPA assay despite having a negative SBA titer. The sera were heat-inactivated and added to the whole blood at a serum dilution of 1:4. After the inoculation of the test strains, samples from the inoculated blood were taken at 0 and 1.5 hours and the CFU/ml was determined.

Example 3

Ex Vivo Passive Protection Bacterimia Assay (PPA) on Stored Sera

An exemplary ex-vivo passive protection bactericidal assay (PPA) of the present disclosure was used to assay the stored pre-immunization and post-immunization sera from 36 healthy adults immunized with three doses of a 3-component vaccine (five antigen vaccine, see materials and methods). Bactericidal activity of these sera against strains NZ989/254 and S3032 were measured as described in materials and methods. These strains were relatively resistant to serum bactericidal activity and opsonophagocytic activity. Each of the sera was diluted 1:4 in whole blood from the non-immune donor identified in example 2. Samples were collected at time 0 and 1.5 hrs after the inoculation of the test strain into a reaction mixture comprising fresh whole blood from non-immune donor and test serum, and CFU/ml determined. For strain NZ98/254, the mean log 10 change in CFU/ml for the 36 pre-immunization sera was −0.12 log 10, which increased to −1.0 log 10 for the respective sera obtained after immunization (P<0.001). The corresponding log 10 changes in CFU/ml for strain S3032 were −0.59 before immunization to −1.69 after immunization (P<0.001).

Example 4

Ex-Vivo Passive Protection Bactericidal Assay (PPA) is Reproducible

Stored pre-immunization and post-immunization sera samples from 14 of the 36 subjects were assayed at different time points over a period of 1 to 3 months using the PPA. The source of whole blood was the non-immune donor identified in example 2. Each of the heat inactivated serum was diluted 1:4 in fresh whole blood. Sera from the 14 subjects are labeled 1 through 14, where A indicates pre-immunization sera and B indicates post-immunization sera. A positive PPA is defined as 0.5 log 10 decrease in CFU/ml at 1.5 hrs after inoculation of bacteria as compared to that of negative control at time 0. FIG. 4, Panels A and B show PPA results using strains NZ98/254 and S3032, respectively. Each serum was assayed three times. With the exception of serum 1A against strain S3032, the results were reproducible for each of the three times a serum was tested in independent experiments performed at three separate occasions.

Example 5

Figure 5A:
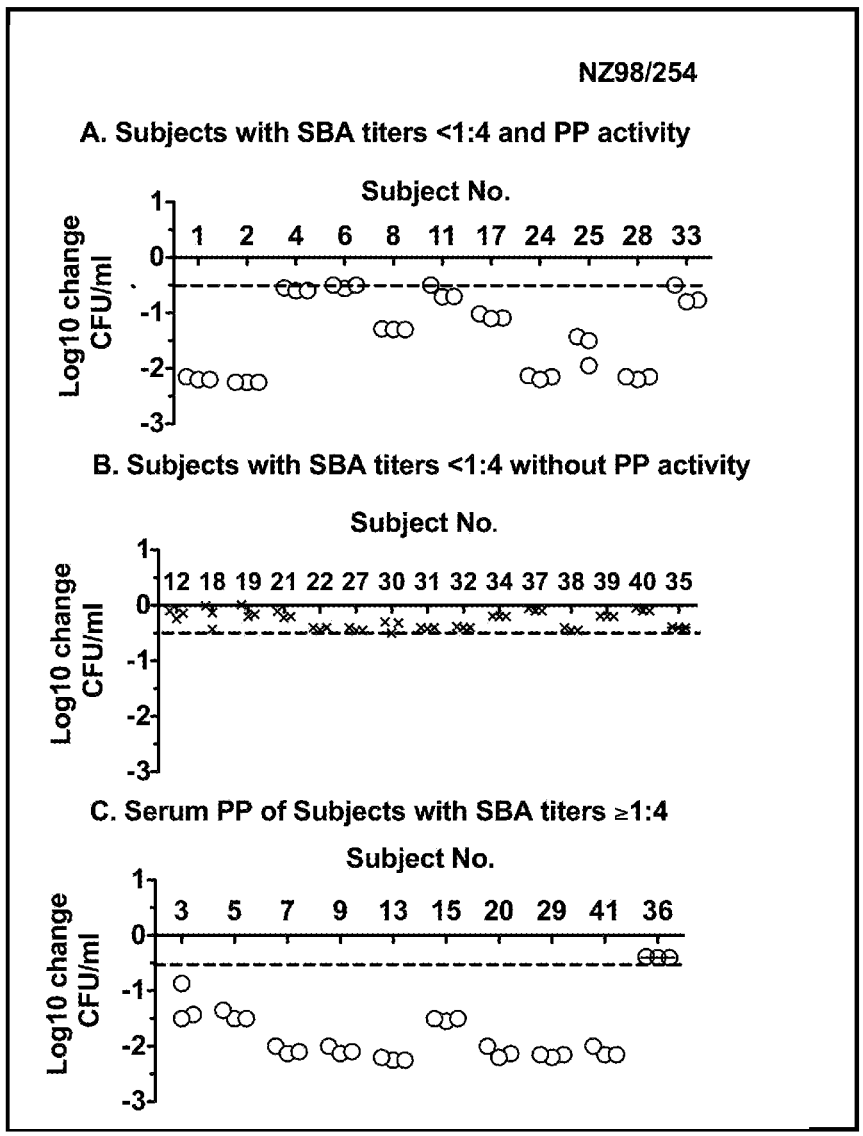

Ex Vivo Passive Protection Bacterimia Assay (PPA) on Sera from Individuals Vaccinated with 3-Component Vaccine Sera from subjects vaccinated with a 3-component vaccine were tested using SBA and PPA on strain NZ98/254. PPA was performed in three independent experiments conducted at three separate occasions. Subjects with SBA titers <1:4 were assayed by PPA. FIG. 5A, Panel A shows that PPA indicates that some subjects with SBA titers <1:4 have bactericidal anti-Neisserial antibodies against strain NZ98/254. Panel B shows that PPA indicates that some subjects with SBA titers <1:4 do not have bactericidal anti-Neisserial antibodies against strain NZ98/254. Panel C is a measurement of bactericidal activity assayed by PPA on sera that have SBA titer ≥1:4. Comparing Panel A to Panel C reveals that PPA measures bactericidal activity in SBA titers <1:4 as well as it measures bactericidal activity in SBA titers <1:4 because the magnitude of the log 10 change was comparable for both SBA titers.

Figure 5B:
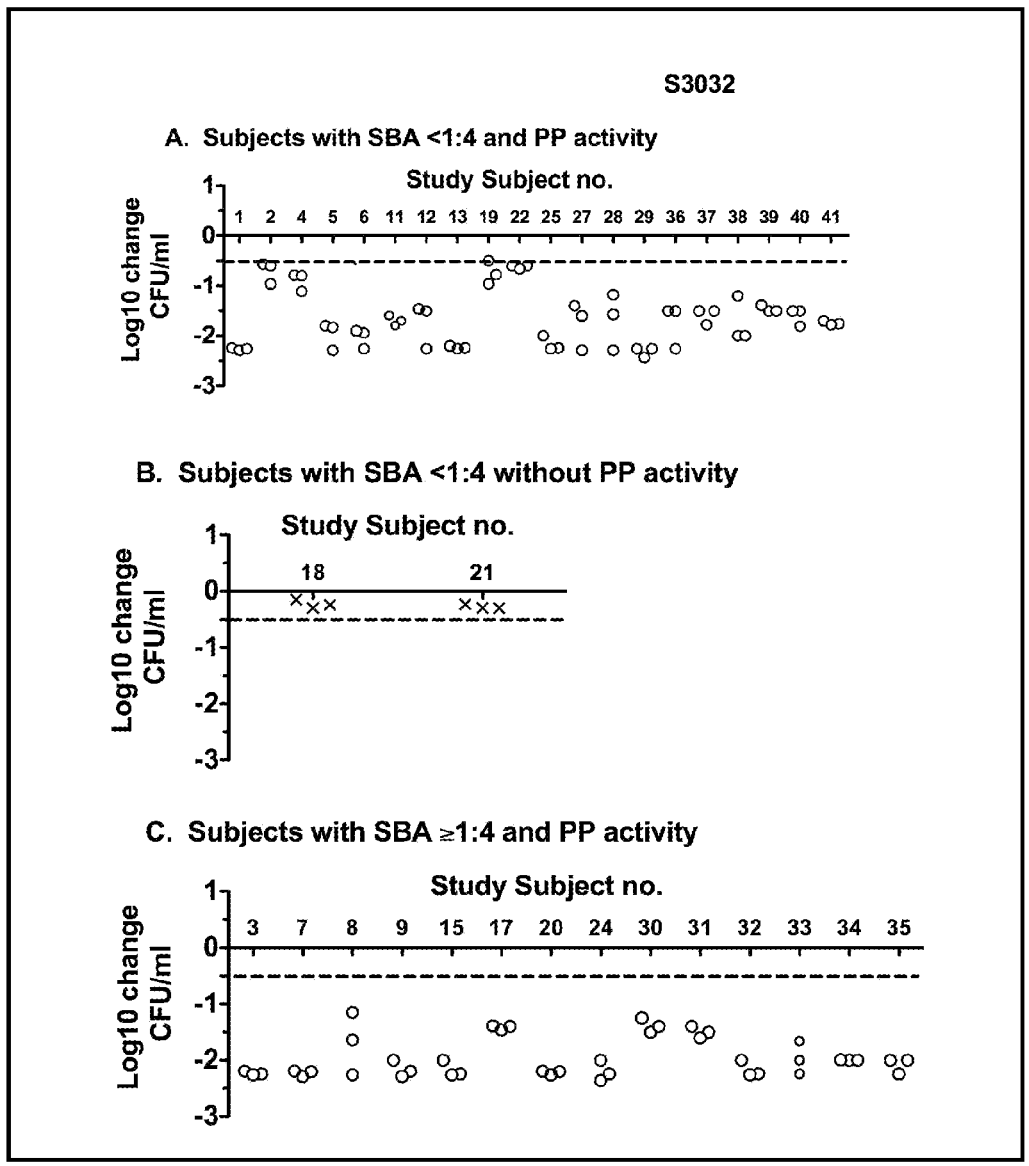

Sera from subjects vaccinated with a 3-component vaccine were tested using SBA and PPA on strain S3032 (FIG. 5B). PPA was performed in three independent experiments. Of the subjects with SBA titers <1:4 and positive PPA, the log 10 change in CFU/ml in the whole blood assay was of similar magnitude as those observed with sera with SBA titers ≥1:4 (FIG. 5B, compare Panel A to Panel C).

Example 6

Comparison of SBA, OPA and PPA

Figure 6:
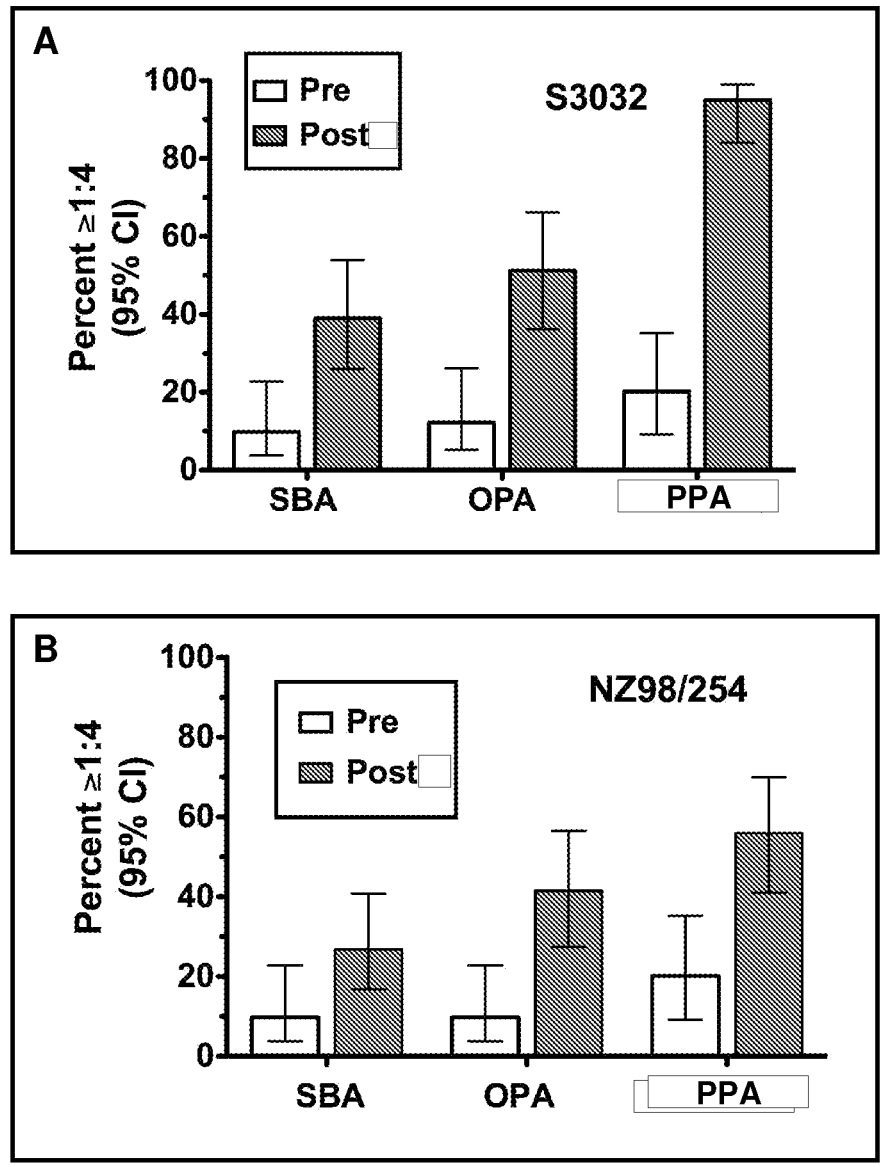

Stored pre-immunization and post-immunization sera from 36 healthy adults immunized with three does of a 3-component vaccine (five antigen vaccine, see materials and methods), were assayed by SBA, OPA and PPA. The sera were diluted 1:4 in each assay. A positive SBA or OPA titer was defined as a 50% decrease in CFU/ml after 1 hour incubation of bacteria as compared with time 0. A positive PPA is defined as 0.5 log 10 decrease in CFU/ml at 1.5 hrs after inoculation of bacteria as compared to that at time 0. As is evident from FIG. 6, PPA is more sensitive than both SBA and OPA. In the post-immunization sera, positive PPA was over 2- to 3-folds more frequent than a SBA titer ≥1:4 against both test strains, NZ98/254 and S3032. Similarly, positive PPA was 1.5- and ~2-folds more frequent than an OPA titer ≥1:4 against test strain NZ98/254 and S3032, respectively. An opsonophagocytic bactericidal titer of ≥1:4 measured with human complement and human PMNs was detected in about 10% to 50% more post-immunization sera than a SBA titer of ≥1:4. Thus, measurement of opsonophagocytic bactericidal activity may be more sensitive than serum bactericidal activity for detecting bactericidal antibody but the incremental advantage of the opsonophagocytic assay was not as large as would be desired.

What is claimed is:

1. A method of detection of bactericidal antibodies effective against a Gram-negative pathogenic bacterium of interest in a biological sample, the method comprising:
   combining in a reaction mixture:
      a biological sample suspected of containing bactericidal antibodies effective against a Gram-negative pathogenic bacterium of interest, wherein the biological sample is human serum or human plasma that is heated to inactivate endogenous complement;

the Gram-negative pathogenic bacterium of interest, wherein the Gram-negative pathogenic bacterium is viable; and fresh human whole blood obtained from a non-immune human donor which does not contain detectable bactericidal antibodies effective against the Gram-negative pathogenic bacterium of interest, wherein the human from which the human serum or the human plasma was obtained is not the non-immune human donor, and wherein said fresh human whole blood contains an anticoagulant that does not significantly affect complement activation or complement activity; and detecting the presence or the absence of the bactericidal antibodies in said sample by assessing viability of said Gram-negative pathogenic bacterium, wherein decreased viability of said Gram-negative pathogenic bacterium in the presence of said biological sample indicates the sample contains the bactericidal antibodies.

2. The method of claim 1, wherein said biological sample is the human serum.

3. The method of claim 1, wherein said biological sample is the human plasma.

4. The method of claim 1, wherein said biological sample in the reaction mixture is a biological pre-immune sample and wherein the method further comprises:

combining in a separate reaction mixture:
a biological post-immune sample suspected of containing the bactericidal antibodies, wherein the post-immune sample and the pre-immune sample are obtained from the same human and wherein the post-immune sample is obtained after administration of an immunogenic composition intended to elicit bactericidal antibodies effective against the Gram-negative pathogenic bacterium to the human, wherein the pre-immune sample and the post-immune sample are heated to inactivate endogenous complement;

the Gram-negative pathogenic bacterium, wherein the Gram-negative pathogenic bacterium is viable; and fresh human whole blood which does not contain detectable bactericidal antibodies effective against the Gram-negative pathogenic bacterium of interest, wherein the fresh human whole blood is obtained from a non-immune human donor, wherein the human from which the human serum or the human plasma was obtained is not the non- immune human donor, and wherein said fresh human whole blood contains an anticoagulant that does not significantly affect complement activation or complement activity; and detecting the presence or the absence of the bactericidal antibodies in said pre-immune sample and in said post-immune sample by assessing viability of said Gram-negative pathogenic bacterium in said samples, wherein the presence of the bactericidal antibodies in the post-immune sample as compared to the pre-immune sample is indicative of the ability of the immunogenic composition administered to the human to elicit the bactericidal antibodies.

5. The method of claim 4, wherein said Gram-negative pathogenic bacterium is a *Neisseria* bacterium and said immunogenic composition comprises a Neisserial antigen.

6. The method of claim 5, wherein said *Neisseria* bacterium is *Neisseria meningitidis*.

7. The method of claim 4, wherein said pre-immune sample and said post-immune sample are a pre-immune serum sample and a post-immune serum sample, respectively.

8. The method of claim 4, wherein the combining of the pre-immune sample in the reaction mixture and the combining of the post-immune sample in the separate reaction mixture is carried out in parallel.

9. A method of screening for an immunogenic composition intended to elicit bactericidal antibodies effective against a Gram-negative pathogenic bacterium of interest, said method comprising:

combining in a first reaction mixture:
a pre-immune biological sample obtained from a human prior to administration of an immunogenic composition intended to elicit bactericidal antibodies effective against a Gram-negative pathogenic bacterium of interest;

the Gram-negative pathogenic bacterium, wherein the Gram-negative pathogenic bacterium is viable; and fresh human whole blood obtained from a non-immune human donor, which does not contain detectable bactericidal antibodies effective against the Gram-negative pathogenic bacterium, wherein the human from which the pre-immune biological sample is obtained is not the non-immune human donor, and wherein said flesh human whole blood contains an anticoagulant that does not significantly affect complement activation or complement activity;

combining in a second reaction mixture:
a post-immune biological sample obtained from said human subject following administration of the immunogenic composition; said fresh human whole blood; and said Gram negative pathogenic bacterium, wherein said Gram-negative pathogenic bacterium is viable; and detecting the presence or the absence of the bactericidal antibodies effective against the Gram-negative pathogenic bacterium in each of the pre-immune and the post-immune biological samples by assessing viability of the Gram-negative pathogenic bacterium:

wherein the pre-immune and the post-immune biological samples are human serum samples or human plasma samples; and wherein the presence of the bactericidal antibodies in the post-immune sample as compared to the pre-immune sample is indicative of the ability of the immunogenic composition administered to the human to elicit the bactericidal antibodies.

10. The method of claim 9, wherein the pre-immune biological sample and the post-immune biological sample are the human serum samples.

11. The method of claim 9, wherein said Gram negative pathogenic bacterium is *Neisseria* bacterium.

12. The method of claim 11, wherein said *Neisseria* bacterium is *Neisseria meningitidis*.

* * * * *

UNITED STATES PATENT AND TRADEMARK OFFICE
CERTIFICATE OF CORRECTION

| | | |
|---|---|---|
| PATENT NO. | : 8,663,940 B2 | Page 1 of 1 |
| APPLICATION NO. | : 13/133907 | |
| DATED | : March 4, 2014 | |
| INVENTOR(S) | : Dan M. Granoff | |

It is certified that error appears in the above-identified patent and that said Letters Patent is hereby corrected as shown below:

In the Specification

In column 1, lines 13-16, please replace "This work was supported by National Institutes of Health grant RO1 AI46464 from the National Institute of Allergy and Infectious Diseases, NIH. The federal government has certain rights in this invention" with -- This invention was made with government support under grant no. AI46464 awarded by the National Institute of Allergy and Infectious Diseases. The government has certain rights in the invention --.

Signed and Sealed this
Thirteenth Day of May, 2014

Michelle K. Lee
*Deputy Director of the United States Patent and Trademark Office*